United States Patent
Nisha et al.

(10) Patent No.: US 11,752,274 B2
(45) Date of Patent: Sep. 12, 2023

(54) INJECTION MONITORING DEVICE AND SYSTEM

(71) Applicants: Sawhney Nisha, New York, NY (US); Singh Kumar Shiv, Liverpool (GB)

(72) Inventors: Sawhney Nisha, New York, NY (US); Singh Kumar Shiv, Liverpool (GB)

(*) Notice: Subject to any disclaimer, the term of this patent is extended or adjusted under 35 U.S.C. 154(b) by 1149 days.

(21) Appl. No.: 16/326,362

(22) PCT Filed: Aug. 17, 2017

(86) PCT No.: PCT/US2017/047427
§ 371 (c)(1),
(2) Date: Feb. 18, 2019

(87) PCT Pub. No.: WO2018/035369
PCT Pub. Date: Feb. 22, 2018

(65) Prior Publication Data
US 2021/0308385 A1    Oct. 7, 2021

Related U.S. Application Data

(60) Provisional application No. 62/376,109, filed on Aug. 17, 2016.

(51) Int. Cl.
*A61M 5/315* (2006.01)
*G16H 20/17* (2018.01)
(Continued)

(52) U.S. Cl.
CPC .... *A61M 5/31573* (2013.01); *A61M 5/31568* (2013.01); *G16H 20/17* (2018.01);
(Continued)

(58) Field of Classification Search
CPC .............. A61M 5/315; A61M 5/31568; A61M 5/31573; A61M 5/31566;
(Continued)

(56) References Cited

U.S. PATENT DOCUMENTS

| 4,248,255 A | 2/1981 | Moore |
| 4,624,659 A | 11/1986 | Goldberg |

(Continued)

FOREIGN PATENT DOCUMENTS

| CA | 2960286 A1 | 3/2016 |
| CN | 1496274 A | 5/2004 |

(Continued)

OTHER PUBLICATIONS

International Preliminary Report on Patentability, PCT/US17/47427, dated Oct. 4, 2018, USPTO, Alexandra, US.
(Continued)

*Primary Examiner* — Tiffany Legette
(74) *Attorney, Agent, or Firm* — Cittone Demers & Arneri LLP; Henry J. Cittone

(57) ABSTRACT

A syringe use monitoring device that can attach to a syringe and detect the type of medication being loaded and measure the force applied to the plunger and thus monitor subsequent delivery of medication and delivery pressure as a substance is being injected, and at least one display and/or alarm can indicate normal and/or abnormal conditions so that feedback can be employed during the injection process is provided.

26 Claims, 5 Drawing Sheets

(51) Int. Cl.
*G16H 40/63* (2018.01)
*A61M 5/31* (2006.01)

(52) U.S. Cl.
CPC ..... *G16H 40/63* (2018.01); *A61M 2005/3126* (2013.01); *A61M 2205/18* (2013.01); *A61M 2205/3331* (2013.01); *A61M 2205/3584* (2013.01); *A61M 2205/502* (2013.01); *A61M 2205/581* (2013.01); *A61M 2205/582* (2013.01); *A61M 2205/583* (2013.01); *A61M 2205/6072* (2013.01)

(58) Field of Classification Search
CPC ...... A61M 2205/6072; A61M 2205/60; A61M 2205/581; A61M 2205/502; A61M 2205/3584; A61M 2205/3331; A61M 2205/18; A61M 2005/3126
See application file for complete search history.

(56) References Cited

U.S. PATENT DOCUMENTS

| | | | |
|---|---|---|---|
| 6,086,569 | A | 7/2000 | Schweizer |
| 2005/0004518 | A1 | 1/2005 | Call |
| 2008/0015406 | A1 | 1/2008 | Dlugos |
| 2008/0243088 | A1 | 10/2008 | Evans |
| 2011/0009821 | A1 | 1/2011 | Jespersen |
| 2013/0123619 | A1 | 5/2013 | Griggs |
| 2013/0226137 | A1 | 8/2013 | Brown |
| 2014/0005950 | A1 | 1/2014 | Groeschke et al. |
| 2014/0081208 | A1 | 3/2014 | Maloney |
| 2014/0324020 | A1 | 10/2014 | Stefansen |
| 2015/0024335 | A1 | 1/2015 | Sabourin |
| 2015/0174342 | A1 | 6/2015 | Mitrosky |
| 2015/0238698 | A1 | 8/2015 | Perry |
| 2015/0257977 | A1 | 9/2015 | Bochenko |
| 2015/0314081 | A1 | 11/2015 | Barere |
| 2016/0259913 | A1* | 9/2016 | Yu ..................... A61M 5/31511 |
| 2017/0312455 | A1 | 11/2017 | Mirov |

FOREIGN PATENT DOCUMENTS

| | | |
|---|---|---|
| CN | 1925885 A | 3/2007 |
| CN | 101198366 A | 6/2008 |
| CN | 101484783 A | 7/2009 |
| CN | 201375731 Y | 1/2010 |
| CN | 102170929 A | 8/2011 |
| CN | 102725011 A | 10/2012 |
| CN | 103120818 A | 5/2013 |
| CN | 103520806 A | 1/2014 |
| CN | 103813819 A | 5/2014 |
| CN | 104582762 A | 4/2015 |
| CN | 205031665 U | 2/2016 |
| CN | 205145299 U | 4/2016 |
| CN | 105813684 A | 7/2016 |
| JP | 2007-267870 A | 10/2007 |
| JP | 2013-521832 A | 6/2013 |
| RU | 2010129479 A | 10/2012 |
| WO | 2015143058 A1 | 9/2015 |
| WO | 2016007935 A2 | 1/2016 |
| WO | 2016071912 A1 | 5/2016 |

OTHER PUBLICATIONS

The International Search Report and the Written Opinion of the International Searching Authority, PCT/US17/47427, dated Nov. 29, 2017, International Search Authority of the US Commissioner for Patents, Alexandria, US.

* cited by examiner

INJECTION MONITORING DEVICE AND SYSTEM

CROSS-REFERENCE TO RELATED APPLICATIONS

This application is the U.S. National Stage of PCT International Patent Application No. PCT/US2017/047427, filed Aug. 17, 2017, which claims benefit to and priority of U.S. Provisional Patent Application No. 62/376,109, filed Aug. 17, 2016, the disclosures of each of which are incorporated herein by reference in their entireties.

FIELD OF INVENTION

The invention is in the field of medical devices and monitoring equipment, more particularly, the field of injection monitoring.

BACKGROUND OF INVENTION

Preliminarily, inclusion of any information or reference citation in this application is not an admission that it constitutes prior art.

Drug errors occur with significant frequency despite multiple checks that have been incorporated over the years. It is estimated that administration errors (excluding wrong-time errors) are frequent, with error rates per dose ranging from 2.4 to 11.1 percent. The cause of such errors is often human error. Some of these drug errors can be fatal and lead to huge emotional burden on the families involved. Drug errors are also a huge economic burden on the health care system.

For example, operating room medication errors continue to occur, many with significant morbidity and/or mortality. Anesthesia professionals in the operating room have a unique role and responsibility in that they are the only medical personnel who prescribe, secure, prepare, administer, and document medications (a process that can take up to 41 steps) usually within a very short time interval. In addition these steps occur in real time, autonomously, often in a distracting environment, and typically without standardized protocols.

The probability of confusion related to drug errors is usually the product of 6 main factors; Sound alike, look alike, location expectation, trust, work flow expectation and work flow trust. In a clinical practice, there are numerous causes for drug errors and these can occur at the time of preparation e.g. choosing wrong drug, wrong dilution/concentration and wrong labeling. They can occur at the time of administration e.g. picking up wrong drug due to fatigue or distraction, wrong dosage due to lack of knowledge or calculation error and incomplete or wrong labeling. Worst of all, despite taking all the right steps in preparing and labeling, the error may be picking up and administering a wrong drug e.g. administering a drug that instead of curing, causes harm and sometimes irreversible harm. Many drug errors can be prevented by standardization, use of technology and change in culture. Standardization like use of standard dilution and labeling for injectable drugs are important but still do not prevent the wrong drug from being administered or human error in calculation or labeling. Use of barcode reader can be a solution but that will only be useful for identifying the drug being loaded and diluted.

Thus, it would be highly advantageous if there were available a device that assists, informs and guides a caregiver through the process of preparing and administering an injectable medication.

SUMMARY OF THE INVENTION

In general, the invention is achieved as follows:

In aspects of the present invention, a monitoring syringe system having one or more predetermined user detection zones, a plunger, and one or more speakers is devised wherein upon a user engaging with the one or more predetermined user detection zones, the monitoring syringe provides medication information, e.g. alerts, in an audible format via the one or more speakers. The system may also provide information it collects during medication preparation and injection to a networked computing system (e.g. one made of smart devices as described herein. In embodiments of this system the functions of information gathering and provision of alerts and medication information may be from other devices than the syringe itself, for example handheld smart devices or on site computing devices.

In further aspects the monitoring system is detachable from the syringe such that the monitoring system may be reusable after disposal of the syringe components of the system.

DETAILED DESCRIPTION OF THE INVENTION

Figure 1:
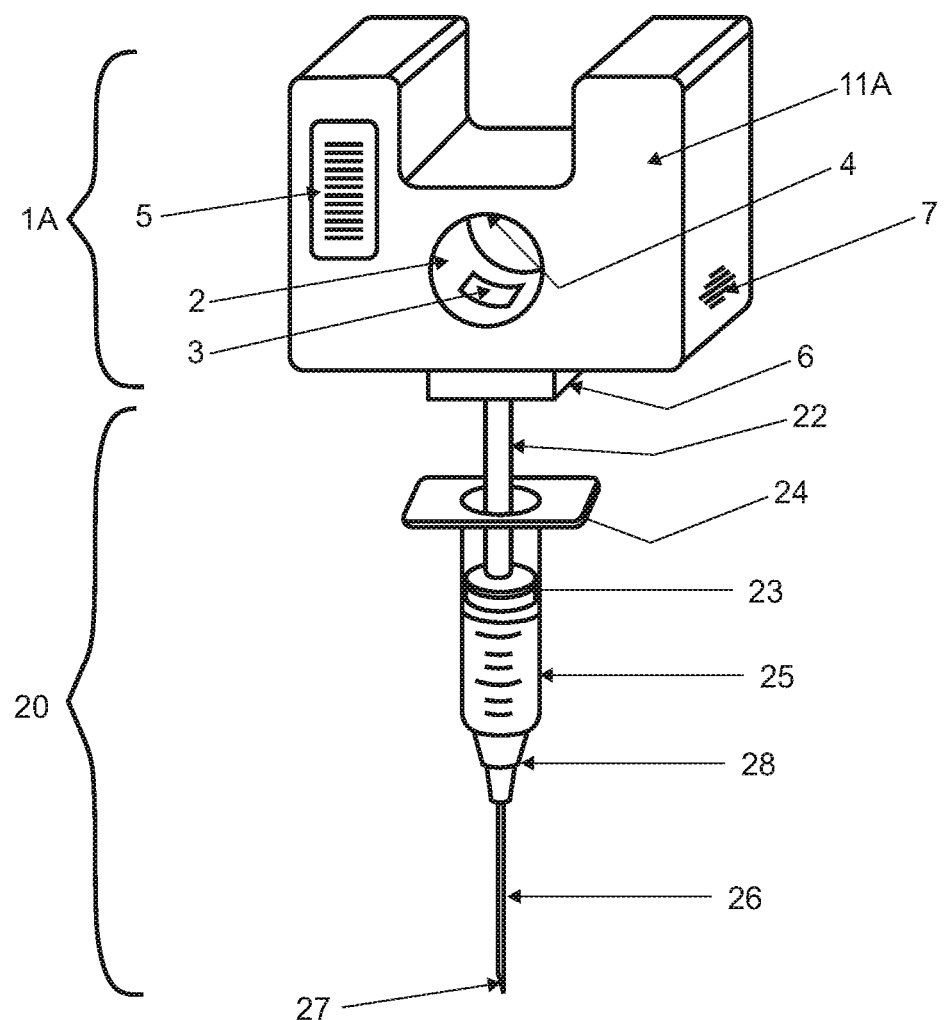
FIG. 1 depicts one embodiment of a syringe use monitoring device attached to the plunger shaft of a syringe.

The present invention is directed, inter alia, to provision of a syringe monitoring system. A syringe monitoring device senses when a user is engaging with the syringe and communicates that engagement to a computer or network of computing devices which then respond with information concerning the type of medication and dosage that should be administered.

A central feature of the invention is the ability of the syringe monitoring device to detect when a syringe is being filled with medication and when it is dispensing medication. By way of overview, in a syringe monitoring system of the invention there are the following capabilities (i) acquisition of medication information for any medication a syringe is to be used with, (ii) detection of the filling of a syringe with medication and (iii) detection of the dispensing of medication from a syringe. Thus, the focus of the present invention is an integrated system that can detect what medication is about to be filled and then detect the dispensing of that medication from the syringe as well as the manner of that dispensing. A significant advantage of the syringe monitoring system is the prevention of medication errors via a system of alerts and confirmations to the user.

One parameter is the identification of a medication to be administered using a variety of methods which are discussed herein. For example, a specific device designed for each medication ("designated device") is provided which can attach to the syringe used to administer that medication. The designated device may be specific for individual drugs, color coded per the ASTM or other standard, and labeled appropriately as would the mating syringe.

Alternatively or in conjunction with the aforementioned designated device, the medicine container (or single use syringe) is equipped with a color coded area, an alpha numeric code, name, QR code, bar code, identifying pattern, RFID, or any combination of these that provide medication information about the medication such as type, name and concentration. A smart device or other networked device ("data acquisition device" for short) having one or more of a camera, information acquisition, RFID reader or scanning function is used to acquire information from the medicine container or single use syringe. In another embodiment, the aforementioned medication information may also be present on a data storage device such as flash memory that is connected to a communications subsystem of the syringe.

In embodiments, the data acquisition device may detect the presence of one or more medication containers within a defined fill area such as a patient's room. For example, the camera can be used to capture an area view of a nurse's tray. Where more than one medicine container is detected within the fill area, the data acquisition device will send information about all of these medicine containers to a networked computing device, either remote or integrated with the data acquisition device. As further discussed herein, information gathered by the data acquisition device is processed and alerts may be generated. In this case for example, an alert that the fill area contains multiple medicine containers can be sent to the user so that the user becomes aware of the potential for a medication error (i.e. the filling of a syringe with the wrong medicine).

A key parameter is a finger detection zone which determines whether a user is engaging with a syringe. The detection of user engagement may trigger a number of events described herein.

Another key parameter is one or more sensors which determine whether a syringe is being filled, referred to herein as "fill application sensors". Such one or more fill application sensors may sense force such as the upward force exerted when a syringe is being filled. The detection of an upward force may trigger a number of events described herein.

A further key parameter is one or more sensors which determine whether a syringe is undergoing an injection action and/or dispensing medication, referred to herein as "force application zones". Such one or more fill application sensors may sense force such as the downward force exerted when a syringe is being injected and/or medication dispensed. The detection of a downward force may trigger a number of events described herein.

In one embodiment, as soon as a designated device is mated to a plunger it is active and a voice command is initiated. An exemplary voice command such as "you are loading Ephedrine 30 mgs in this 10 mL syringe." As soon as a thumb is placed into the designated device, it activates an administration alert—for example "do you wish to administer Ephedrine to the patient."

Referring now to another exemplary method of using an embodiment of the present invention, when first clipped on to a plunger of the syringe, a device advises on the exact dose and concentration to be used, stating for example: "Ephedrine, 30 mg to be diluted to 10 mls with Saline". On insertion of thumb, it alerts the user by: (1) stating what the user is going to administer: "you are going to deliver adrenaline to your patient" and (2) stating the dose "the dose is 1 mL of 1 in 10,000 adrenaline." Dosage information may be omitted if desired.

The device may also be incorporated into a hospital security, communication, paging, and/or alert system, so that indications, warnings, and information from the device can be transmitted remotely, via either wireless or wired means. For example, a remote nurse station, physician device (pager, tablet, smart watch, smartphone, desktop computer, augmented reality headset/glasses, etc.) may receive a notification that a nurse is preparing to administer drugs using the device. The dosing and drug information can be sent remotely, and prior to start of the administration by the nurse, the remote caregiver (head or charge nurse, attending physician, etc.) can sent an alert back to the device to (1) proceed with the drug administration, or (2) to stop the drug administration due to an erroneous dosage or drug type. The alert to the administrating nurse can be audible, vibratory, haptic, and/or visual.

In addition to a remote signal, a local device, such as a loudspeaker, smart television display, bedside display, or computing device in the vicinity of the patient may be coupled to the device, via for example, a wired connection such as a USB cable or a wireless connection such as a Bluetooth or other wireless connection. Prior to administration, any alert given by the device may also be transmitted to a local device for output or display, so that a loud volume audible warning is given, or a large letter visual display is provided to all those present in the vicinity of the patient.

Furthermore, the device may be coupled to a smartphone application such that an administering nurse can receive a haptic/vibration alert via their smartphone as a warning or indication of the dosage and drug type. In addition, any other relevant party may link their smartphone via the application to the patient's specific device in order to monitor drug administration.

The application can include reporting and tracking so that a patient's drug delivery history can be audited by nurse/physician, drug type, dosage, time of day, etc.

Pressure sensors in the device may also be used to continuously measure pressures during injection of drugs, for example, into sensitive tissues that may be damaged by high pressures. One such area is administration of local anesthetic (LA) around nerves. Injection of LA under high pressure can cause damage to the nerve. A device called SARAS (Safe Regional Anaesthesia System) later described in the document is one such embodiment.

In addition to pressure sensors, the device may include various types of triggers, including, but not limited to optical, physiological-dependent, and mechanical, as well as a remote trigger (i.e., allowing a remote attending physician to unlock the device so that a local nurse can administer the drug).

The device can be re-usable, or configured for a one-time, disposable use. The device can include an LED or otherwise digital display, as well as speakers. In another embodiment, the device can include a region for printed matter or an adhesive label to indicate the dosage and drug information.

In an embodiment, the device is open from the top for easy usage of the syringe. For example, the device can be a U-shaped device. For different drugs, the device may be color-coded and with either same color LED or standard one color LED for all drugs. Furthermore, in another embodiment, the device may be used with non-syringe products like syrup bottles or non-medical products, for example, hazardous materials used in various medical and non-medical related industries.

Referring now to a pressure sensing embodiment of the present invention, a "Safe Regional Anesthesia System" (SARAS) is provided. The SARAS both displays the pressure applied during injection and transmits the pressure data to a remote computing device for recording and having a display for monitoring. The SARAS is shaped to fit onto a plunger, thus mimicking the hand feel users are accustomed to when injecting. SARAS is ideally suited to usage during the administration of nerve blocks. SARAS is capable of multiple uses, the pressures sensed are electronic, more accurate and can be calibrated easily, and the device can display and record the injection pressures for documentation as a medico-legal document and is therefore useful for closed claims. SARAS can be linked to a computing network for real time display of injection pressures on monitors for data processing to display injection pressures graphically.

In these embodiments the pressure of the fluid being injected is not directly being measured. This avoids having the surface of a pressure sensor come directly in contact with the substance being injected. Were a sensor to be located within the flow of liquid medication, the sensor would have to be thoroughly cleaned after every use as well as be completely non-chemically reactive with the substance being injected. A no contact method of pressure determination is more desirable. The force of injection has several components, and pressure is defined as the force per unit area. If the area of the plunger seal and barrel internal diameter is A and the back force produced by the action of the plunger seal on the barrel is Ff and the force applied by the finger during injection is Fa, then the pressure in the syringe barrel will be $(Fa-Ff)/A=Pi$, where Pi is the injection pressure. If the force of injection is steadily applied and relatively slow, there will be very little if any plunger velocity dependent force components to be figured in, so only the static force at constant threshold velocity is needed to obtain the resultant injection pressure Pi. Alternatively, corrections can be applied when the device is calibrated under test conditions, such as the use of accurate pressure sensors in an expandable container or vessel during test injections.

Referring now to FIG. 1, an embodiment of a syringe use monitoring device attached to the plunger shaft of a syringe is provided. Shown is a removable syringe use monitoring device 1A portion and the syringe 20. In this embodiment the removable syringe use monitoring device 1A portion comprises the housing 11A in which is located the finger insertion zone 2. When a finger is inserted into the finger insertion zone 2 the finger insertion action 81 is initiated, and this will be described in more detail later. When the syringe 20 is being filled with a drug during the syringe filling action 82, the finger of the person administering a drug is applying a force in the upward direction, and this triggers the fill application sensor 4 which is located at the top of the finger insertion zone 2. This syringe filling action 82 can trigger a number of events described herein. When the finger is applying downward force to the force application zone 3, this triggers injection action 83, which will be described herein. Shown is plunger shaft 22 and plunger seal 23 located within barrel 25. Barrel 25 attaches to hub 28 from which protrudes needle shaft 26. At the tip of needle shaft 26 is the bevel 27 which is what punctures the skin or surface of what is being injected. At the top portion of the barrel 25 is the top collar 24. Also shown is the plunger attachment zone 6 located at the bottom of the housing 11A, and one embodiment of this is shown in more detail in FIG. 3. FIG. 1 also shows bar graph 5 and speaker 7.

Figure 2:
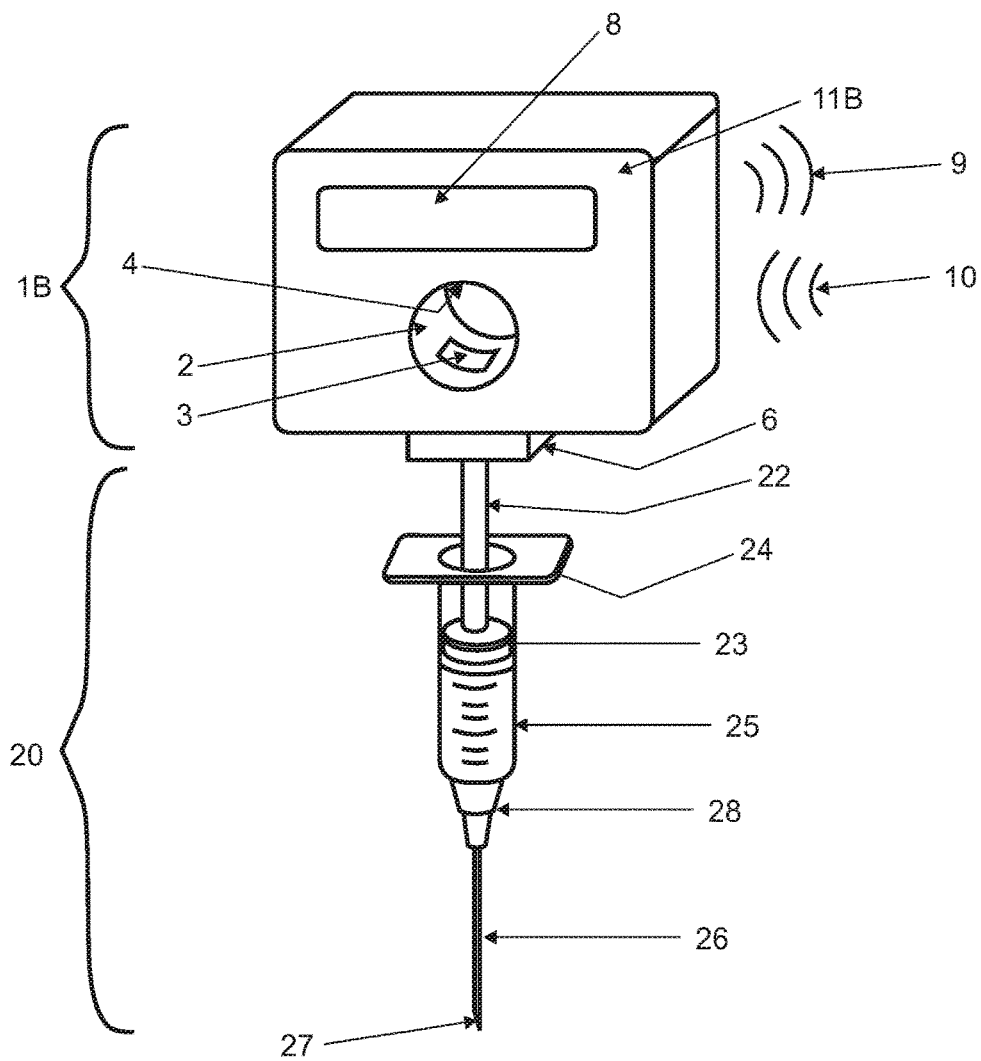
FIG. 2 depicts another embodiment of a syringe use monitoring device attached to the plunger shaft of a syringe.

Referring now to FIG. 2, it depicts another embodiment of a syringe use monitoring device attached to the plunger shaft of a syringe. Shown is the removable syringe use monitoring device 1B portion and the syringe 20. In this embodiment the removable syringe uses a monitoring device 1B portion which comprises the housing 11B in which is located the finger insertion zone 2. When a finger is inserted into the finger insertion zone 2 the finger insertion action 81 is initiated, and this will be described in more detail later. When the syringe 20 is being filled with a drug during the syringe filling action 82, the finger of the person administering a drug is applying a force in the upward direction, and this triggers the fill application sensor 4 which is located at the top of the finger insertion zone 2. This syringe filling action 82 can trigger a number of events described herein. When the finger is applying downward force to the force application zone 3, this triggers injection action 83, which will be described herein. Shown is plunger shaft 22 and plunger seal 23 located within barrel 25. Barrel 25 attaches to hub 28 from which protrudes needle shaft 26. At the tip of needle shaft 26 is the bevel 27 which is what punctures the skin or surface of what is being injected. At the top portion of the barrel 25 is the top collar 24. Also shown is the plunger attachment zone 6 located at the bottom of the housing 11B, and one embodiment of this will be shown in more detail in FIG. 3. FIG. 1 also shows display 8 and wireless transmitted signal 9 and wireless received signal 10. Different features are shown in FIG. 1 and FIG. 2 but it should be understood that either embodiment can contain bar graph 5, speaker 7, display 8, and any method of communication, wireless being shown for example in FIG. 2. A general system is shown schematically in FIG. 7

Figure 3A:
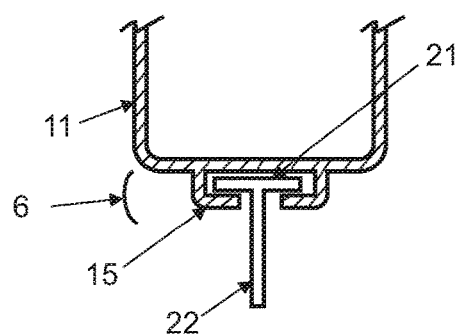
FIGS. 3A and 3B depict a close up of one embodiment of a cross-section the plunger attachment zone of a syringe use monitoring device.
Figure 3B:
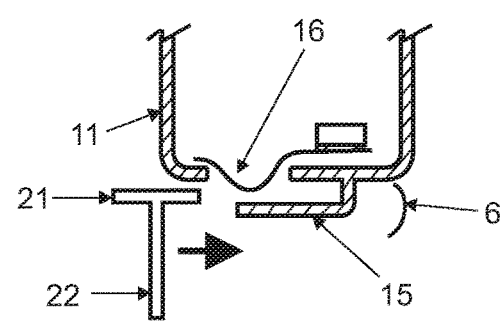

Referring now to FIGS. 3A and 3B, they depict a close up of one embodiment of a cross-section the plunger attachment zone 6 of a syringe use monitoring device. FIG. 3A shows a cross-section of a general housing 11, the plunger top gripper 15 attached to the bottom of the general housing 11. Shown in the attached position is the plunger top 21 and plunger shaft 22. FIG. 3B is a cross-section view at right angles to the view depicted in FIG. 3A. In this depiction the plunger top 21 and plunger shaft 22 is not connected but shows the direction of attachment. General housing 11 and the plunger top gripper 15 is shown. Also shown is the syringe attachment sensor 16, which in this embodiment can be a switch that is depressed when the plunger top 21 and plunger shaft 22 is inserted into plunger attachment zone 6.

Figure 4:
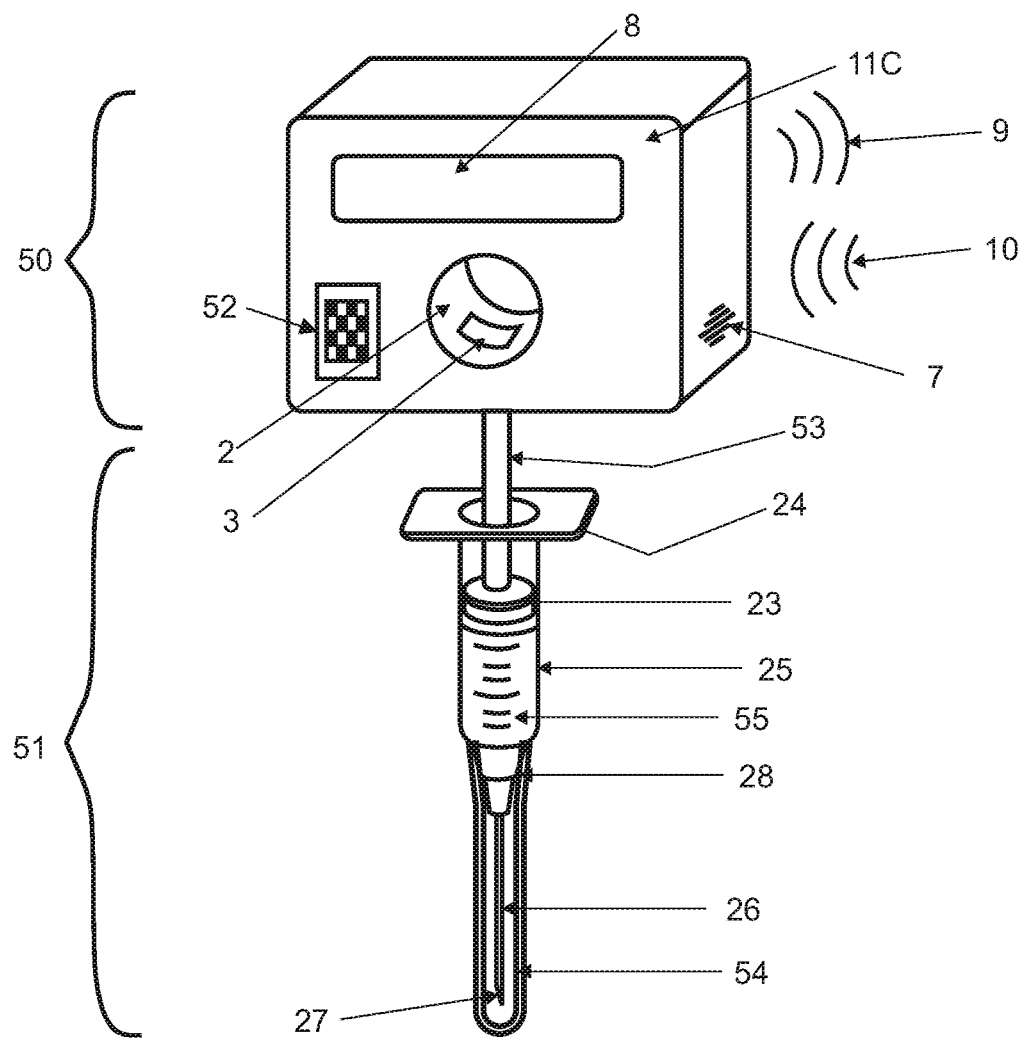
FIG. 4 depicts an embodiment of the invention that is incorporated within the plunger for single use injections, with a drug already in the syringe.

Referring now to FIG. 4, it depicts an embodiment of the invention that is incorporated within the plunger for single use injections, with a drug already in the syringe. Shown is the syringe use monitoring device with integral plunger 50 and the syringe portion 51. In this embodiment the syringe use monitoring device with integral plunger 50 portion comprises the housing 11C in which is located the finger insertion zone 2. When a finger is inserted into the finger insertion zone 2 the finger insertion action 91 is initiated, and this will be described in more detail later. This may also turn on or cause power to be applied to the syringe use monitoring device with integral plunger 50. In this embodiment, the syringe is already filled with drug or substance 55 so there is no filling operation as with the embodiments depicted in FIG. 1 and FIG. 2. There may also be a separate on switch or button (not shown), and the device may also be turned on when removed from its packaging prior to use. When the finger is applying downward force to the force application zone 3, this triggers injection action 93, which will be described herein. Shown is the integral plunger shaft 53 and plunger seal 23 located within barrel 25. Barrel 25 attaches to hub 28 from which protrudes needle shaft 26. At the tip of needle shaft 26 is the bevel 27 which is what punctures the skin or surface of what is being injected. This also comes with the cap 54, which would be removed prior to injection. At the top portion of the barrel 25 is the top collar 24. Also shown is display 8, speaker 7, and wireless transmitted signal 9 and wireless received signal 10. Also shown is the visible ID 52, which can take many forms including but not limited to at least one color coded area, at least one alpha-numeric code and/or name, a QR code, a bar code, at least one unique identifying pattern, or any combination in whole or part of any of the above. There may also be a bar graph 5 as shown in FIG. 1, and any method of communication, wireless being shown for example only in FIG. 4 and FIG. 2. A general system is shown schematically in FIG. 7

Figure 5:
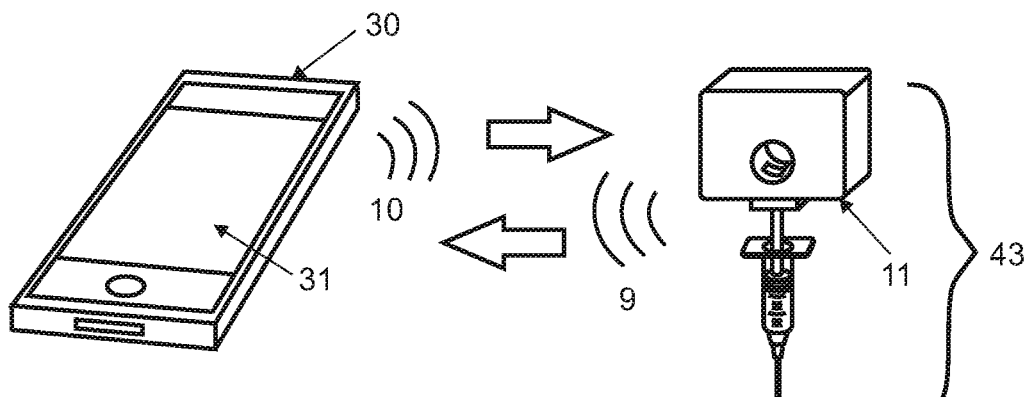
FIG. 5 depicts the communication between a syringe use monitoring device and a smart device.

Referring now to FIG. 5, it depicts communication between a syringe use monitoring device 43 and a smart device 30 with smart device display 31. Shown is wireless transmitted signal 9 and wireless received signal 10, which enables bidirectional wireless communication between these two devices. The smart device display 31 may be used as the display for the generalized syringe use monitoring device 43 as a cost saving feature. Also shown here is a generalized housing 11. In this embodiment the smart device contains a library of drugs and/or substances. With specialized software the two devices work together to become a powerful system, adding the full power of a smart device's computational, display, and communication ability.

Figure 6:
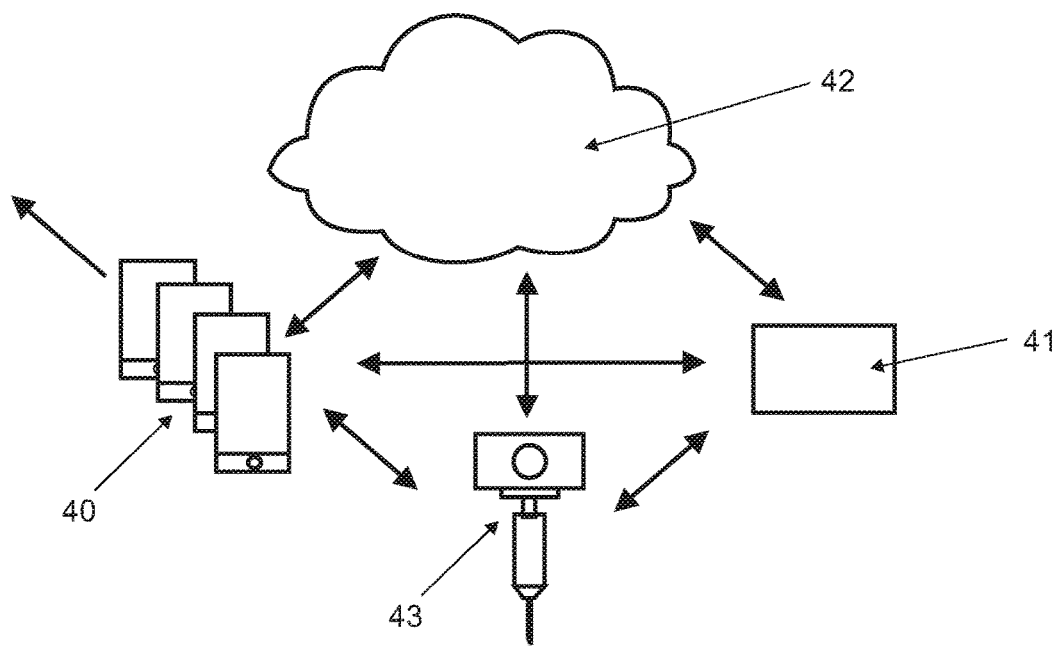
FIG. 6 depicts a typical system incorporating a syringe use monitoring device and communication between at least one smart device, a central processor incorporating a master data base, and the cloud.

Referring now to FIG. 6, it depicts a system incorporating a syringe use monitoring device 43 and communication between at least one smart device 40, a central processor with master data base 41, and a cloud computing environment 42 ("cloud"). In this embodiment the syringe use monitoring device 43 can communicate directly with either at least one smart device 40, the central processor with master data base 41, or with the cloud 42. At least one smart device can 40 be any number of smart devices communicating with any other number of at least one smart device 40 in any number of topological configurations. At least one smart device 40 can also communicate with a central processor with master data base 41, the cloud 42, or at least one generalized syringe use monitoring device 43. In this embodiment the cloud 42 can communicate with at least one smart device 40, with the central processor with master data base 41, or at least one generalized syringe use monitoring device 43. And in this embodiment the central processor with master data base 41 can communicate with at least one smart device 40, with the cloud 42, and with at least one generalized syringe use monitoring device 43. In this manner any part of the system can communicate either directly with any other part of the system or it can communicate through other elements within the system to get to other elements within the system. The data base can be distributed amongst many smart devices as well, and in the cloud. In a hospital or an entire health care network this creates a powerful tool for incorporating injectable, inhalable, or ingestible medications within a tracking and drug dispensing data base which can not only track medication schedules and dosages, but help prevent errors of incorrect dispensing of medication and dosages.

Figure 7:
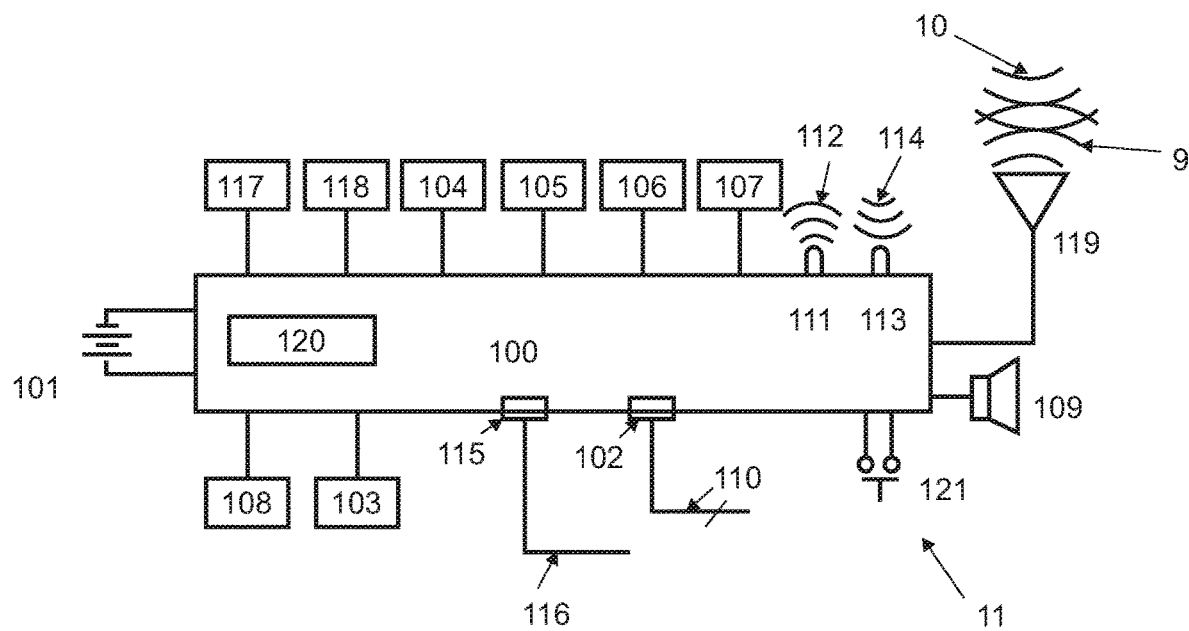
FIG. 7 shows a block diagram of a general system from which different embodiments can be derived. There are many embodiments that can be implemented and remain within the spirit of the invention.

Referring now to FIG. 7, it shows a block diagram of a general system from which different embodiments can be derived. There are many embodiments that can be implemented and remain within the spirit of the invention. The heart of the system is the microprocessor 100 and support electronics 120, all of which is contained with a generalized housing 11. Battery 101 powers the system, and power can be initiated by the insertion of a syringe as previous stated, by the removal from packaging, and with a switch or pushbutton 121. Battery 101 can be a rechargeable battery which can enable the generalized housing and the syringe use monitoring device to be used over and over to dispense many medications. Recharging power can be obtained via electrical connector 102, which can also enable communication over wire 110. The plunger attachment sensor 103 can also enable the application of power to the syringe use monitoring device. Fill sensor 104 can be an input to microprocessor 100.

Load cell 105, force sensing resistor 117, or strain gauge 118 can be used to provide the applied force when appropriately calibrated. When force is known the pressure can be determined because pressure equals force/unit area. Communication can be accomplished via several methods including a wireless transceiver 119. The transceiver 119 can be an integrated transceiver or it can be created using a transmitter and a receiver, and any configuration will for convenience be called a transceiver 119. Communication can also occur vial infrared (IR) signals. IR emitter 111 can generate emitted IR signal 112 and IR sensor 113 can receive IR received signal 114. Fiber optic communication can be achieved by receiving and/or sending signals through a fiber optic connector 115 that is connected to a fiber optic cable 116. A display can be a bar graph 106, an LCD display 107, or an LED display 108. As stated previously, signals can be communicated to a smart device which can be used as the display device as well. Sound in the form of spoken audio messages, audio alarms, sirens, frequencies, or any sound can be emitted via speaker 109. The support electronics 120 can perform signal filtering, amplification, level shifting, level offset, modulation, and other functions.

Figure 8:
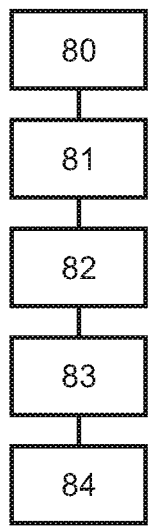
FIG. 8 is a flowchart showing the different operations and actions for removeable syringe use monitoring device as depicted in FIG. 1 and FIG. 2

Referring now to FIG. 8, a flowchart showing the different operations and actions for embodiments of a removable syringe use monitoring device, for example as depicted in FIG. 1 and FIG. 2. Syringe attachment action 80 initiates wake-up of and/or power application to the syringe use monitoring device and creation of at least one first indication and/or alert and/or spoken message. The finger insertion action 81 causes the creation of at least one second indication and/or alert and/or spoken message. The syringe filling action 82 causes the creation of at least one third indication and/or alert and/or spoken message. The injection action 83 causes the creation of at least one fourth indication and/or alert and/or spoken message. This fourth indication and/or alert can be at least one of at least one emergency alert, alarm, at least one sound and/or audible frequency that indicates the injection is occurring within acceptable limits, at least one sound and/or audible frequency that is proportional to force applied within said force application zone. The upload data 84 can be an optional function depending upon the embodiment, but the upload data 84 can be at least one communication to at least one smart device, a central processor with a master data base, at least one cloud, or at least one other syringe use monitoring device.

Figure 9:
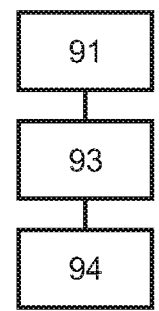
FIG. 9 is a flowchart showing the different operations and actions for a syringe use monitoring device with integral plunger as depicted in FIG. 4

Referring now to FIG. 9, a flowchart showing the different operations and actions for an embodiment of a syringe use monitoring device with integral plunger, such as that depicted in FIG. 4 is depicted. The finger insertion action 91 causes the creation of at least one first indication and/or alert and/or spoken message. The injection action 93 causes the creation of at least one second indication and/or alert and/or spoken message. This second indication and/or alert can be at least one of at least one emergency alert, alarm, at least one sound and/or audible frequency that indicates the injection is occurring within acceptable limits, at least one sound and/or audible frequency that is proportional to force applied within said force application zone. The upload data 94 can be an optional function depending upon the embodiment, but the upload data 94 can be at least one communication to at least one smart device, a central processor with a master data base, at least one cloud, or at least one other syringe use monitoring device.

Figure 10:
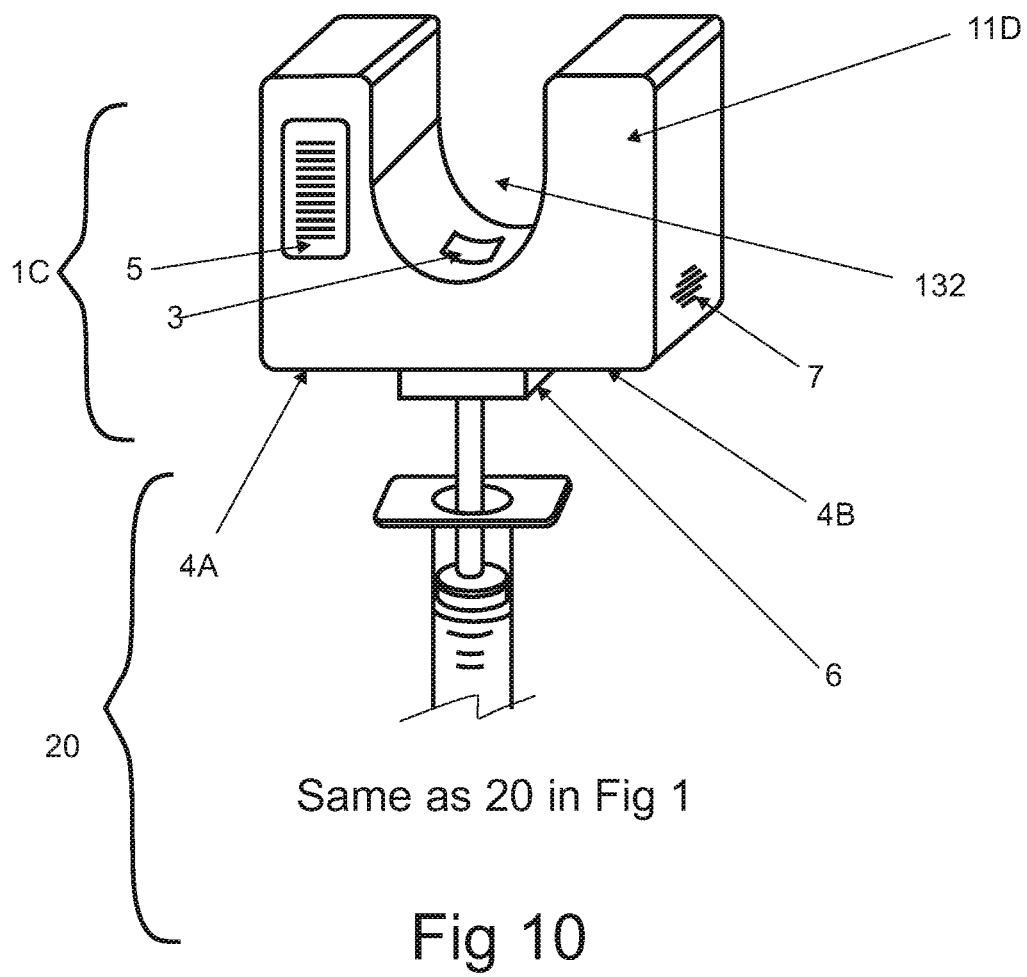
FIG. 10 depicts a U-shaped embodiment of a syringe use monitoring device attached to the plunger shaft of a syringe.

Referring now to FIG. 10, it depicts an embodiment of a syringe use monitoring device attached to the plunger shaft of a syringe. In this U housing 11D there is a U-shaped open channel U finger insertion zone 132 as opposed to the circular finger insertion zone 2 of FIG. 1. Shown is the removable syringe use monitoring device 1C portion and the syringe 20. In this embodiment the removable syringe use monitoring device 1C portion comprises the U housing 11D in which is located the U finger insertion zone 132. When either a finger is inserted into the U finger insertion zone 132 or one or more fingers apply upward force to the bottom fill application sensor 4A and/or the bottom fill application sensor 4B, the finger insertion action 81 is initiated, which has already been described. When the syringe 20 is being filled with a drug during the syringe filling action 82, one or more fingers of the person administering a drug is applying a force in the upward direction, and this triggers the bottom fill application sensor 4A and/or the bottom fill application sensor 4B which is located at the bottom of the U housing 11D. This syringe filling action 82 can trigger a number of events described herein. After the syringe filling action 82, when the finger is applying downward force to the force application zone 3, this triggers injection action 83, which has already been described. Other than the open channel and U shape, the only difference between this embodiment and the embodiment of FIG. 1 is that now the syringe filling action 82 is sensed by bottom fill application sensor 4A and/or bottom fill application sensor 4B. Also shown is plunger shaft 22 and plunger seal 23 located within barrel 25. Barrel 25 attaches to hub 28 from which protrudes needle shaft 26. At the tip of needle shaft 26 is the bevel 27 which is what punctures the skin or surface of what is being injected. At the top portion of the barrel 25 is the top collar 24. Also shown is the plunger attachment zone 6 located at the bottom of the U housing 11D, and one embodiment of this has been shown in FIG. 3. FIG. 1 also shows bar graph 5 and speaker 7.

This U housing 11D configuration can be combined with the embodiment of FIG. 4, which depicts an embodiment of the invention that is incorporated within the plunger for single use injections, with a drug already in the syringe. In this embodiment there would be no 4A bottom fill application sensor or 4B bottom fill application sensor because the syringe portion 51 would already be filled. When a finger is inserted into the U finger insertion zone 132, the finger insertion action 91 is initiated as already described herein. This may also turn on or cause power to be applied to the syringe use monitoring device. Since in this embodiment the syringe is already filled with drug or substance 55, there is no filling operation as with the embodiments depicted in FIG. 1, FIG. 2, and FIG. 10. There may also be a separate on switch or button (not shown), and the device may also be turned on when removed from its packaging prior to use. When the finger is applying downward force to the force application zone 3, this triggers injection action 93, which has been described herein. As already described in FIG. 4, there would be the integral plunger shaft 53 and plunger seal 23 located within barrel 25. Barrel 25 attaches to hub 28 from which protrudes needle shaft 26. At the tip of needle shaft 26 is the bevel 27 which is what punctures the skin or surface of what is being injected. This also comes with the cap 54, which would be removed prior to injection. At the top portion of the barrel 25 is the top collar 24. Also shown is display 8, speaker 7, and wireless transmitted signal 9 and wireless received signal 10. Also shown is the visible ID 52, which can take many forms including but not limited to at least one color coded area, at least one alpha-numeric code and/or name, a QR code, a bar code, at least one unique identifying pattern, or any combination in whole or part of any of the above described in any of the figures. There may also be a bar graph 5 as shown in FIG. 1, and any method of communication, wireless being shown for example only in FIG. 4 and FIG. 2. An embodiment of the system is shown schematically in FIG. 7, and many combinations can be implemented and remain within the spirit of the invention.

Referring now to subsystems that may be used in constructing various embodiments discussed herein or envisioned from the present disclosure, load cells take a variety of forms and in embodiments can be off the shelf or custom designed and integrated into the force sensing subsystem. They can be similar to the 100 gram micro load cell RB-Phi-203 by Phidgets™, which is rated at 100 uv/volt when supplied with between 3 and 10 volts, and is typically used in conjunction with a Wheatstone bridge amplifier such as the Phidgets Phi-107 or other custom designed amplifiers employing operational amplifiers. Another load cell can be the 780 gram RB-Phi-117. These load cells typically have high repeatability, accuracy, and precision. For instance, the RB-Phi-117 has a precision of 0.05% of full scale, a non-linearity of 0.05% of full scale, repeatability of 0.05% of full scale, and a creep of 0.1% of full scale over a 30 minute period.

The S410 and S415 are miniature low profile button load cells manufactured by Strain Measurement Devices™. They come in 0.24, 0.5, and 1 KG force sensing ranges. They are wired in a four resistive element bridge configuration, with four wires, with each wire being the intersection of two adjacent resistive elements of the bridge.

The S251 and S252 are miniature platform low profile load cells measuring maximum forces in the 0.4 to 22 pound range. These are 3000 ohm thin film bridge configurations, and ideal for medical applications such as the invention. The S215 model is an ultra low profile miniature single point load cell featuring a 10,000 ohm bridge for low power consumption and high accuracy.

For example, voltage can be applied across two wires of a four wire bridge, with a differential voltage being obtained from the other two wires or nodes. This differential voltage is then amplified typically using an instrumentation amplifier commonly available as one of many possible integrated circuits. For example, two possible IC amplifiers can be based on the LM308 precision operational amplifier on the higher end to the LM324 quad op amp on the lower end, or anything in between. Hundreds of op-amps can be chosen from manufacturers such as Texas Instruments™, National Semiconductor™, Fairchild™, and Analog Devices™, to name a few. Amplified, offset, and buffered voltages proportional to force can then be fed to an A/D converter that can be a stand-alone component or integrated within a microprocessor package for subsequent quantification and processing. For example, the many processors from Microchip can accommodate analog inputs in conjunction with sufficient processing power to perform all the necessary control functions required by the invention. A/D resolutions vary from 8 to 16 bits in what is now lower end processors, and it is not uncommon to have resolutions of 16 to 32 bits as with the ATSAM4E8C and IC24FJ128GC010 processors from Microchip™.

Load cells can also be constructed with strain gauge wires that change resistance as a function of load. These wires are typically attached between two surfaces that move relative to one another, causing a displacement that applies force to the wire and subsequently stretches the wire. As long as the wire remains within a linear region of deformation, the resistance will change as a function of deformation, and will produce repeatable results.

Piezo load cells or strain gauge sensors can range from the expensive, such as the Model 740B02 sensor from PCB Piezotronics MTS systems corp, to the very inexpensive. They can be made inexpensively and calibrated individually, and can operate accurately enough. In a very simple implementation acoustic indicators such as those produced by Velleman can be sandwiched between a plate and the point where a finger can apply force. Piezo outputs produce a voltage as a function of the rate of change of load application, and it is therefore wise to integrate this signal to produce a measure of force applied, and the pressure this relates to. This integration can take the form of an analog integration performed by any one of hundreds of configurations employing low drift operational amplifiers, or the integration can be performed by digitally sampling the piezo output signal after amplification and buffering.

Component linear strain gauges are also available, such as the SGT-1000-TY series and the SGK-L series strain gauges from Omega. Resistance and corresponding resistance change can be calculated by measuring current and voltage, or by measuring frequency and corresponding frequency change in a voltage controlled oscillator. The SGT-2DD series consists of four shear gauges on a single carrier plate. Two half bridges can be used to form one full Wheatstone bridge. All methods above can easily be implemented by someone skilled in analog circuit design.

Force Sensing Resistors FSRs, such as the Polulu model 1696, are commonly available and change resistance as a function of the force applied. These can be off the shelf components or manufactured as a result of printing or silk screening. The resistance can be measured and the FSR calibrated to yield a resultant force. These tend to be less accurate than strain gauges, but accuracy and repeatability can be achieved with appropriate calibration and not depart from the spirit of the invention.

Bluetooth transceivers for use in embodiments, are now ubiquitous and commonly available from many sources. Transmission range is variable as are the features. A few commercially available off the shelf Bluetooth transceivers are:

1a) BT832F extended range Bluetooth low energy (BLE) 5 module available from Grid Connect™

2a) BT832X extended range Bluetooth low energy (BLE) 5 module available from Grid Connect™

3a) Bluetooth Serial Adapter Firefly DTE NOPS from Grid Connect™

4a) Phillips FR3 Bluetooth transceiver module from Medshop™

Other modules or chip sets that could be incorporated as a subsystem within the circuitry are the following to name a few:

1b) Wireless Bluetooth V2.0 RS232 TTL Transceiver module available from Hobbytronics™

2b) Wireless Serial 4 Pin Bluetooth RF transceiver Module HC-06 RS-232, made by LankaTronics™, and available from Astral Robot 3b) Wireless Bluetooth RF Transceiver Module HC-05, with a range of about 30 feet, made by LankaTronics™

4b) LB3431 Wireless Bluetooth Serial Tranceiver Module from FastTeck™

Connection to these are similar, and many require a minimum four wire attachment to the system. Typically there is a ground and Vcc+line to power the module (which can be 3.3 volts, 5 volts, or other voltages), a pin to receive signals (often called the Rx pin), and a pin to transmit signals (often called the Tx pin). There are many transceivers available. To conserve power a power control system can be incorporated within the system so power is only applied to the transceiver when communication is required. Some transceivers incorporate an enable line to wake the transceiver up from a low power or sleep mode.

In embodiments of the present invention, RFID chips are utilized. RFID chips and subsystems are commercially available and used for anything from product identification in stores and inventory in warehouses, to monitoring animals on farms, pets, people, files, and other things that require identification. Tags fall into two classes, active tags possessing power in the form of a battery, and passive tags that are unpowered and receive power from an electromagnetic field generated external to the tag. The passive tag receives electromagnetic radiation and transforms this received energy into a form that enables a chip incorporated within the tag to transmit an encoded signal back through the receiving antenna that received the power to energize the tag in the first place. This encoded ID signal can be of almost any length, encompassing any amount of information such as including but not limited to medication or chemical content, recommended dosage, expiration date, manufacturing date, manufacturer, production lot, contraindications, and/or any other information. This information can be receive by the transmitting device and information can be obtained about the contents of a container upon which the RFID tag is placed. A typical scenario is as follows: a medication is going to be loaded into the syringe. The RFID tag is stimulated and sends contents data to the syringe. The syringe receives this information and informs the user as to the contents and/or other useful information. The user loads the syringe with the medication in preparation for injection. The user injects the medicine, and the injection occurs in accordance with proper parameters as previously defined herein based on the information provided by the device to the user.

An exemplary RFID subsystem is the Allen Bradley™ model 56RF-UB-IP. Another possible RFID subsystem is the FPX3-869-20 by Radiometrix™. There are many subsystems that can be incorporated within the invention and remain within the spirit of the invention.

In communications between devices of the present invention, the sending of data and/or signals, the receiving of data and/or signals, or the sending and receiving of data and/or signals between at least one sender and at least one receiver occurs. Any form of communication can be utilized to achieve the objectives of the present invention. Any mode of communication can incorporate the encryption and decryption of data.

For example, communication may be the sending of analog signals, digital signals, or both. Communication can occur over a wire, as in one digital device output to one digital device input, such as what would commonly occur when one microprocessor or digital component or system sends data to another in either direction. A wire can be considered any conductive trace that directly connects any component to any other component. Data can also be buffered to be sent over greater distances or to many devices. Data can be serial, parallel, or both. Communication can be optical, as in sending data or signals over a fiber optic transmission line. Optical communication can involve the use of any optical transmitter that creates light of any frequency that can be received by an optical sensor that receives light of any frequency, such as IR, visible, or UV.

For example, many microprocessors now incorporate A/D (analog to digital) converters, D/A (digital to analog) converters, or both. External A/D converters may also accept analog signals which in turn can be fed to a microprocessor and D/A converters may be fed from the microprocessor to produce an analog signal from a digital number or stream of digital numbers. An example of analog communication would be a sensor producing an analog signal, having that signal amplified and/or scaled and/or offset with circuitry, and this signal then being sent via a communication line to an analog input in a microprocessor or other component or components where it would subsequently be quantified into a digital number for further processing.

Another form of wireless communication may employ at least one of the following: RFID, near field NFC device, unpowered NFC chip tags, Bluetooth in 2400-2480 mhz band, Bluetooth in bands now known or unknown, frequency hopping spread spectrum based systems, Wifi, Zigbee IEEE 802.15 standard, communication for use in industrial, scientific, and medical bands utilizing 686 MHZ in Europe and/or 915 MHZ in the US and/or 2.4 GHZ in most worldwide jurisdictions.

Communication can also occur acoustically by emitting acoustic waves from one location in space and receiving acoustic energy in another location in space.

An exemplary communication subsystem may be a subsystem incorporating the components necessary to cause communication, and can be any device that enables communication in any mode such as over a wire, wireless, optical, acoustic, or any other means by which information can be sent from at least one location in space to at least one other location in space. For example the receipt of data and/or transmission of data is envisioned.

Exemplary smart devices can be a mobile device, which is a generic term used to refer to a variety of portable devices that allow people to access data and information. A mobile device (also known as a handheld computing device, handheld device, handheld computer or simply handheld) may also be hand-held computing device, which can have a display screen which can also have a touch input and/or a miniature keyboard.

A smart device may be a handheld computing device, and may have an operating system (OS), and may run various types of application software, known as apps. Most handheld devices may also be equipped with at least one of WI-FI, Bluetooth and GPS capabilities that allow connections to the Internet, other computing networks and/or other Bluetooth capable devices such as an automobile or microphone headset. A smart device may also incorporate at least one communication receiver device and/or the at least one communication transmitter device and/or the at least one communication transmitter/receiver device employing at least one of Wi-Fi, radio wave and/or electromagnetic radiation, and/or Bluetooth. A camera and/or media player feature for video or music files may also be found on these devices along with a battery power source. Other types of mobile devices include tablet computers. As in a personal digital assistant ("PDA"), the input and output are often combined into a touch-screen interface, smartphones, PDAs, Enterprise Digital Assistants, any or all of which may offer integrated data capture devices such as barcode reading capability, RFID, optical, optical in conjunction with QR codes, Optical Character Recognition, smart card readers, and/or at least one Touch Code reader.

A smart device can be more than one smart device. It can be a mobile device as mentioned above, a laptop, tablet, smart watch, mainframe computer, desktop computer, server, and/or super computer, and can contain or be connected to at least one camera, reader device, input device and/or scanner, a projection device and/or system. A user smart device may have internet or other network connection capability and employ or have resident at least one web browser or similar software to access said network.

A smart device may be any device with a capacitive touch screen such as including but not limited to a smart phone, Ipad, Iphone, Android, tablet, touch screen in a car, touch sensitive screen on any device and/or a custom capacitive and/or touch sensitive screen. The smart device and touch screen can be activated by a touch code and/or human touch and/or capacitive element and/or conductive element as found on including but not limited to: a smart phone, Iphone, Ipad, Android, a computer, a tablet, a reader, a vending machine. Furthermore, a smart device is capable of any of the following but not limited to communicating via wifi and/or electromagnetically, taking pictures and/or video, displaying images, entering and displaying data, near field communication, Bluetooth communication.

A smart device can further be or comprise of at least one of at least one communication receiver device and/or the at least one communication transmitter device and/or the at least one communication transmitter/receiver device employing at least one of Wi-Fi, radio wave and/or electromagnetic radiation, and/or Bluetooth.

There can be any number of smart devices in the chain or network, forming serial and parallel paths for information to flow in one or more directions, and all the smart devices are individually and collectively referred to as the "smart device". The smart device can talk either directly to the internet, to at least one other smart device that in turn communicates to the internet, and/or directly or through at least one other smart device to at least one master smart device possessing at least one data base that is updated and/or the source of data to be used in at least one other destination.

A smart device comprises in whole or in part of the following components listed in no particular order: at least one microprocessor possessing at least one core; at least one memory; at least one display; at least one means to input data; wherein said at least one means to input data is at least one of at least one camera, a touch screen, a keyboard, at least one form of wireless communication, at least one form of communication via at least one fiber optic cable, at least one form of communication via at least one wire connected to at least one mechanical connector with at least one electrical contact; at least one transceiver configured to communicate with at least one other smart device and/or with a server and/or a network capable of connecting to the internet; said components programmed to do the following: sending at least one formatted list to at least one data base and/or master data base resident in at least one physical location; receiving at least one e-mail and or data; generating at least one report. Software needed to control the system's operations, actions and functions may be coded in applicable programming language such as Java, C, C++, Python or the like as dictated by the smart devices and network selected in a particular embodiment.

A touch code is a conductive area of a particular shape and/or pattern that can be uniquely decoded to produce one of many possible states. The touch code can be at least one of a series of bars of varying sizes, circles of various sizes and angular relationships to one another, rectangular shapes, and/or any geometric shapes that can be quantified and decoded into one of a multiplicity of states. The conductive area and/or areas are not limited to the printing of conductive inks and can be any electrically conductive material that can extend the capacitive effect of a person or entity in contact with the touch screen of at least one smart device.

Electronics may be passive components, active components, analog electronics, digital electronics, hybrid electronics, voltage regulators, integrated circuits, sensors of any kind, light emitting components, and the interconnections between them. Electronics can be used to perform any electronic system function including but not limited to biasing, current limiting, generating at least one voltage from at least one other voltage, signal gain which can be voltage amplification and/or current amplification, signal scaling, signal offset, signal filtering, timing and generation. An electronic subsystem may be at least one of or perform at least one of the following functions: receiver, transmitter, modulator, demodulator, voltage regulator, signal processor, signal acquisition, signal quantification, signal digitation, analog signal generation, display information, sound generator, convert energy from one form to another, acquire data, process data, store data, A display subsystem or monitor may be an LED display, a bar graph display, an LCD display, any method of displaying visual information along a line or within an area, a projection system that projects information or imagery upon at least one surface. The information can be presented as any image that can be perceived by a human including but not limited to numbers, letters, mathematical symbols, symbols that can represent any information including but not limited to medical, biometric, chemical, pharmaceutical, physical, concentration, viscosity, PH, density, volume, mass, temperature, pressure, force, time, color, frequency, voltage, current, charge, power, magnetic, any atomic and/or subatomic parameter. Information can be presented in the form of a graph of any dimensionality.

A venue can be any place or location including but not limited to a hospital, clinic, private office, mobile hospital, any location where medication can be administered or dispensed, school, church, pharmacy, home, apartment, condominium, co-op, public housing, shelter, assisted living facility, nursing home, rehabilitation center.

Referring now to yet other embodiments of the invention devices are provided as follows:

A. A syringe use monitoring device comprising:
a housing and support structure;
a plunger attachment zone attached to or incorporated within said housing or support structure, said attachment zone removably attaches to a syringe plunger top or removably attaches to said syringe plunger top and a syringe barrel;
a trigger region in which a finger or appendage is inserted or pressed against; a force application zone located within said trigger region;
at least one power source;
support electronics comprising at least one of electronics, at least one electronic subsystem, at least one microprocessor that generates at least one output and receives at least one input; a syringe attachment sensor;
at least one sensor that senses at least one of: the presence and/or proximity of said finger or appendage, application of at least one force in at least one direction applied by said finger or appendage within and to said force application zone;
at least one signal generated by said at least one sensor and/or at least one other signal generated by said support electronics that receives said at least one signal generated by said at least one sensor;
a communication subsystem;
at least one indication that is at least one of at least one image displayed on a display element and/or display subsystem, at least one mechanical output and/or motion produced, at least one audio and/or speech indication, wherein said indication indicates at least one of:
at least one normal condition, wherein said normal condition is a condition that operates within at least one normal range of operation that is between at least one upper limit of at least one parameter and at least one lower limit of said at least one parameter,
at least one status,
at least one identification of at least one of:
at least one substance,
at least one of a patient, person or body part thereof, animal or body part thereof, a living thing or a part thereof,
at least one object,
at least one time,
at least one history comprising at least one parameter recorded at at least one first time and at least one second time,
at least one location,
at least one venue,
at least one element or item or entry on at least one menu,
at least one data,
at least one data located and/or retrieved from at least one database,
at least one other piece of information;
at least one alert generator that generates at least one alert as a result of at least one abnormal and/or dangerous condition, said at least one abnormal and/or dangerous condition being or being derived from or generated as a result of said at least one signal and/or said at least one other signal and/or said at least one output, said at least one abnormal and/or dangerous condition being at least one of user settable and/or selectable threshold, automatically selectable threshold, selectable threshold as a result of data received from at least one database via at least one means of communication, at least one customized data that is at least one of: patient specific, demographic specific, at least one population comprising at least two entities, at least one parameter.

AA. The syringe use monitoring device of embodiment A wherein said at least one sensor is at least one of a load cell, a force sensing resistor, at least one strain gauge at least one optical emitter emitting at least one frequency and at least one optical sensor that receives said at least one frequency, at least one switch that activates with the application of at least one force, at least one acoustic energy sensor, at least one spring displacement registering at least one force, wherein said at least one spring displacement is measured and produces at least one electronic signal that is proportional to said at least one force.

BB. The syringe use monitoring device of embodiment A further comprising at least one image identifier located on the container and/or vial containing the substance being filled into a syringe attached to said syringe use monitoring device for determining the contents to be injected, said at least one image identifier being at least one of the following:
- at least one color coded area;
- at least one alpha-numeric code and/or name;
- a QR code;
- a bar code;
- at least one unique identifying pattern;
- any combination in whole or part of any of the above.

CC. The syringe use monitoring device of embodiment BB wherein said at least one image identifier is identified employing the following steps:
using the camera on a smart device to image or take a picture of said at least one image identifier;
running image identification software resident on said smart device to perform at least one recognition process to yield a unique identification code;
using said unique identification code as an address to a file in at least one list; identifying a substance and/or drug listed in said file;
obtaining at least one data associated with said substance and/or drug;
causing communication of said at least one data between said smart device and said syringe use monitoring device;
said syringe use monitoring device produces said at least one indication and a corresponding display and/or alert.

DD. The syringe use monitoring device of embodiment A executing the following steps and/or actions:
syringe attachment action that initiates wake-up of and/or power application to said syringe use monitoring device and creation of at least one first indication and/or alert and/or spoken message;
finger insertion action that causes the creation of at least one second indication and/or alert and/or spoken message;
syringe filling action that causes the creation of at least one third indication and/or alert and/or spoken message;
injection action that causes the creation of at least one fourth indication and/or alert and/or spoken message, said fourth indication and/or alert being at least one of at least one emergency alert, alarm, at least one sound and/or audible frequency that indicates the injection is occurring within acceptable limits, at least one sound and/or audible frequency that is proportional to force applied within said force application zone.

EE. The syringe use monitoring device of embodiment A executing the following steps and/or actions:
syringe attachment action that initiates wake-up of and/or power application to said syringe use monitoring device and creation of at least one first indication and/or alert and/or spoken message;
finger insertion action that causes the creation of at least one second indication and/or alert and/or spoken message;
syringe filling action that causes the creation of at least one third indication and/or alert and/or spoken message;
injection action that causes the creation of at least one fourth indication and/or alert and/or spoken message, said fourth indication and/or alert being at least one of at least one emergency alert, alarm, at least one sound and/or audible frequency that indicates the injection is occurring within acceptable limits, at least one sound and/or audible frequency that is proportional to force applied within said force application zone;
at least one communication to at least one smart device, a central processor with a master data base, at least one cloud, at least one other syringe use monitoring device.

FF. The syringe use monitoring device of embodiment A wherein said support electronics enables power to be switched on or for power to be enabled by the action of attachment of a syringe to said plunger attachment zone.

GG. The syringe use monitoring device of embodiment A further comprising at least one data base, wherein said at least one data base is at least one of part of or incorporated within at least one of at least one central computer system, a stand-alone computer, at least one smart device, at least one cloud and/or at least one cloud-based data base.

HH. The syringe use monitoring device of embodiment A wherein said syringe use monitoring device is used during at least one of an intravenous injection, an injection within an artery, an intramuscular injection, a subcutaneous injection, an injection into a nerve and/or nerve sheath and/or any region contained within the nerve sheath, an injection into a nerve ganglion, an injection into an organ, an injection into the brain, an injection into bone or any location contained within bone, an injection in any cavity or space within a body.

JJ. The syringe use monitoring device of embodiment A wherein said communication subsystem is at least one of at least one wireless transmitter subsystem, wireless receiver subsystem, wireless transceiver subsystem, at least one infrared emitter and at least one infrared sensor, at least one wire connecting at least one smart device to said syringe use monitoring device, at least one fiber optic cable connecting at least one smart device to said syringe use monitoring device.

KK. The syringe use monitoring device of embodiment A further comprising at least one message that indicates what at least one starting mass and/or volume is and at least one quantity of at least one substance that must be added to said at least one starting mass and/or volume to create at least one final injectable substance and/or drug.

LL. The syringe use monitoring device of embodiment A wherein said communication subsystem is used to perform a one way and/or two way wired and/or wireless communication incorporated into at least one of hospital security, communication between said at least one syringe use monitoring device and at least one smart device, paging device, alert system, a central processor with a master data base, at least one cloud.

MM. A syringe use monitoring device comprising:
a housing and support structure;
an integrated plunger permanently attached to or incorporated within said housing or support structure;
a syringe subsystem comprising a barrel, a plunger shaft, a plunger seal that seats within said barrel, a top collar, a needle shaft, a bevel, a hub, and a cap.
a substance and/or drug contained within said barrel;
a trigger region in which a finger or appendage is inserted or pressed against; a force application zone located within said trigger region;
at least one power source;
support electronics comprising at least one of electronics, at least one electronic subsystem, at least one microprocessor that generates at least one output and receives at least one input; at least one sensor that senses at least one of: the presence and/or proximity of said finger or appendage, application of at least one force in one direction applied by said finger or appendage within and to said force application zone;

at least one signal generated by said at least one sensor and/or at least one other signal generated by said support electronics that receives said at least one signal generated by said at least one sensor;

a communication subsystem;

at least one indication that is at least one of at least one image displayed on a display element and/or display subsystem, at least one mechanical output and/or motion produced, at least one audio and/or speech indication, wherein said indication indicates at least one of:

at least one normal condition, wherein said normal condition is a condition that operates within at least one normal range of operation that is between at least one upper limit of at least one parameter and at least one lower limit of said at least one parameter, at least one status, at least one identification of at least one of:

at least one substance, at least one of a patient, person or body part thereof, animal or body part thereof, a living thing or a part thereof, at least one object, at least one time and/or time of administering, at least one history comprising at least one parameter recorded at at least one first time and at least one second time, at least one location, at least one venue, at least one element or item or entry on at least one menu, at least one data, at least one data located and/or retrieved from at least one database, at least one other piece of information;

at least one alert generator that generates at least one alert as a result of at least one abnormal and/or dangerous condition, said at least one abnormal and/or dangerous condition being or being derived from or generated as a result of said at least one signal and/or said at least one other signal and/or said at least one output, said at least one abnormal and/or dangerous condition being at least one of user settable and/or selectable threshold, automatically selectable threshold, selectable threshold as a result of data received from at least one database via at least one means of communication, at least one customized data that is at least one of: patient specific, demographic specific, at least one population comprising at least two entities, at least one parameter.

AA1. The syringe use monitoring device of embodiment MM wherein said at least one sensor is at least one of a load cell, a force sensing resistor, at least one strain gauge at least one optical emitter emitting at least one frequency and at least one optical sensor that receives said at least one frequency, at least one switch that activates with the application of at least one force, at least one acoustic energy sensor, at least one spring displacement registering at least one force, wherein said at least one spring displacement is measured and produces at least one electronic signal that is proportional to said at least one force.

BB1. The syringe use monitoring device of embodiment MM further comprising at least one image identifier located on said housing and support structure that identifies the contents to be injected, said at least one image identifier being at least one of the following: at least one color coded area;

at least one alpha-numeric code and/or name;

a QR code;

a bar code;

at least one unique identifying pattern;

any combination in whole or part of any of the above.

CC1. The syringe use monitoring device of embodiment BB1 wherein said at least one image identifier is identified employing the following steps:

using the camera on a smart device to image or take a picture of said at least one image identifier;

running image identification software resident on said smart device to perform at least one recognition process to yield a unique identification code;

using said unique identification code as an address to a file in at least one list; identifying a substance and/or drug listed in said file;

obtaining at least one data associated with said substance and/or drug;

causing communication of said at least one data between said smart device and said syringe use monitoring device;

said syringe use monitoring device produces said at least one indication and a corresponding display and/or alert.

DD1. The syringe use monitoring device of embodiment MM executing the following steps and/or actions:

finger insertion action that causes the creation of at least one first indication and/or alert and/or spoken message;

injection action that causes the creation of at least one second indication and/or alert and/or spoken message, said second indication and/or alert being at least one of at least one emergency alert, alarm, at least one sound and/or audible frequency that indicates the injection is occurring within acceptable limits, at least one sound and/or audible frequency that is proportional to force applied within said force application zone.

EE1. The syringe use monitoring device of embodiment MM executing the following steps and/or actions:

finger insertion action that causes the creation of at least one first indication and/or alert and/or spoken message;

injection action that causes the creation of at least one second indication and/or alert and/or spoken message, said second indication and/or alert being at least one of at least one emergency alert, alarm, at least one sound and/or audible frequency that indicates the injection is occurring within acceptable limits, at least one sound and/or audible frequency that is proportional to force applied within said force application zone.

at least one communication to at least one smart device, a central processor with a master data base, at least one cloud, at least one other syringe use monitoring device.

GG1. The syringe use monitoring device of embodiment MM further comprising at least one data base, wherein said at least one data base is at least one of part of or incorporated within at least one of at least one central computer system, a stand-alone computer, at least one smart device, at least one cloud and/or at least one cloud-based data base.

HH1. The syringe use monitoring device of embodiment MM wherein said syringe use monitoring device is used during at least one of an intravenous injection, an injection within an artery, an intramuscular injection, a subcutaneous injection, an injection into a nerve and/or nerve sheath and/or any region contained within the nerve sheath, an injection into a nerve ganglion, an injection into an organ, an injection into the brain, an injection into bone or any location contained within bone, an injection in any cavity or space within a body.

JJ1. The syringe use monitoring device of embodiment MM wherein said communication subsystem is at least one of at least one wireless transmitter subsystem, wireless receiver subsystem, wireless transceiver subsystem, at least one infrared emitter and at least one infrared sensor, at least one wire connecting at least one smart device to said syringe use monitoring device, at least one fiber optic cable connecting at least one smart device to said syringe use monitoring device.

KK1. The syringe use monitoring device of embodiment MM further comprising at least one message that indicates what at least one starting mass and/or volume is and at least one quantity of at least one substance that must be added to said at least one starting mass and/or volume to create at least one final injectable substance and/or drug.

LL1. The syringe use monitoring device of embodiment MM wherein said communication subsystem is used to perform a one way and/or two way wired and/or wireless communication incorporated into at least one of hospital security, communication between said at least one syringe use monitoring device and at least one smart device, paging device, alert system, a central processor with a master data base, at least one cloud.

NN. An inhaler monitoring device comprising:
a housing and support structure;
a reservoir containing a quantity of a substance and/or drug to be inhaled;
a metering pump that dispenses a controlled dosage through the action of depressing a trigger and/or piston;
a trigger region on top of said trigger and/or piston in which a finger or appendage is inserted or pressed against;
a force application zone located within said trigger region;
at least one power source;
support electronics comprising at least one of electronics, at least one electronic subsystem, at least one microprocessor that generates at least one output and receives at least one input; at least one sensor that senses at least one of: the presence and/or proximity of said finger or appendage, application of at least one force in at least one direction applied by said finger or appendage within and to said force application zone;
at least one signal generated by said at least one sensor and/or at least one other signal generated by said support electronics that receives said at least one signal generated by said at least one sensor;
a communication subsystem;
at least one indication that is at least one of at least one image displayed on a display element and/or display subsystem, at least one mechanical output and/or motion produced, at least one audio and/or speech indication, wherein said indication indicates at least one of:
at least one normal condition, wherein said normal condition is a condition that operates within at least one normal range of operation that is between at least one upper limit of at least one parameter and at least one lower limit of said at least one parameter,
at least one status,
at least one identification of at least one of:
at least one substance,
at least one of a patient,
at least one object,
at least one time,
at least one history comprising at least one parameter recorded at at least one first time and at least one second time,
at least one location,
at least one venue,
at least one element or item or entry on at least one menu,
at least one data,
at least one data located and/or retrieved from at least one database,
at least one other piece of information;
at least one alert generator that generates at least one alert as a result of at least one abnormal and/or dangerous condition, said at least one abnormal and/or dangerous condition being or being derived from or generated as a result of said at least one signal and/or said at least one other signal and/or said at least one output, said at least one abnormal and/or dangerous condition being at least one of user settable and/or selectable threshold, automatically selectable threshold, selectable threshold as a result of data received from at least one database via at least one means of communication, at least one customized data that is at least one of: patient specific, demographic specific, at least one population comprising at least two entities, at least one parameter.

As used herein, the term "and/or," when used in a list of two or more items, means that any one of the listed items can be employed by itself, or any combination of two or more of the listed items can be employed. For example, if a device is described as containing components A, B, and/or C, the composition can contain A alone; B alone; C alone; A and B in combination; A and C in combination; B and C in combination; or A, B, and C in combination.

Although preferred embodiments of the present invention have been described herein it will be understood by those skilled in the art that the present invention should not be limited to the described preferred embodiments. Rather, various changes and modifications can be made within the spirit and scope of the present invention.

The invention claimed is:

1. A monitoring device comprising: a housing having one or more user detection zones, a syringe, having a tube and a plunger connected to said housing or integrally molded as part of said housing, said syringe being connected to a needle, one or more displays, speakers or displays and speakers, and a detector which receives information concerning a one or more of a medication and a patient; a communications system which receives and transmits information to a network or computing device wherein the information received comprises medication information and the information transmitted comprises medical administration information; wherein upon a user engaging with the one or more user detection zones, the monitoring device provides medication information via the one or more displays, speakers or displays and speakers wherein said detector is selected from a group consisting of RFID receivers, QR code readers, bar code readers, or digital cameras.

2. The device of claim 1, wherein the one or more user detection zones is a force sensitive zone.

3. The device of claim 1, wherein the one or more user detection zones is a pressure sensitive zone.

4. The device of claim 1, wherein the one or more user detection zones detects that the syringe is being filled by detecting a force indicative of upwards motion of the plunger.

5. The device of claim 1, wherein the one or more user detection zones detects that the syringe is being injected by detecting a force indicative of downwards motion of the plunger.

6. The device of claim 1, wherein said device has one or more finger sockets, having a lower and upper region, and the lower or upper region has the one or more user detection zones.

7. The device of claim 1, wherein the detector is physically separate from the communications subsystem.

8. The device of claim 1, wherein the communications subsystem is physically separate from the detector.

9. The device of claim 1, wherein the one or more displays, speakers or displays and speakers are physically separate from the rest of the device.

10. The monitoring syringe system device of claim 1 wherein the one or more displays, speakers or displays and speakers are selected from a group consisting of visual displays, monitors, LCD screens, or audio speakers.

11. The device of claim 1, wherein the syringe is attachable and detachable.

12. The device of claim 1 wherein the one or more user detection zones is or further comprises a proximity sensor.

13. The device of claim 1 further comprising:
a detector which receives information concerning a medication;
a communication subsystem which transmits or transmits and receives information to a network or computing device, wherein the information transmitted comprises medical information and the information received comprises medical administration information or medical administration information and warnings.

14. The device of claim 1 further comprising:
a pressure sensor which resides within the syringe and which provides a visual indication of the pressure.

15. The device of claim 1 further comprising:
a force sensor which detects the amount of force applied to the syringe's plunger.

16. The device of claim 15, wherein the force sensor is selected from a group consisting of a load cell, force sensing resistor, strain gauge, or spring or material having a spring constant.

17. A medical data collection system comprising: the device of claim 1 further comprising,
(a) a bidirectional wireless communications device, and
(b) a computing system, wherein the computing system:
(i) has access to drug and substance information,
(ii) communicates with the device of claim 1 to receive information concerning the drug or substance being administered,
(iii) accesses the drug and substance information to retrieve information associated with the received information, and
(iii) provides some or all of retrieved information concerning the drug or substance being administered to a user via one or more of visual or audio components.

18. The system of claim 17, wherein said drug and substance information resides on one or more of (i) a computing device or network in wireless or wired communication with the computing system or (ii) on the computing system itself.

19. The system of claim 17, wherein the received information is selected from a group consisting of: drug or substance identity, drug or substance administration requirements, drug or substance contraindications, injection pressure data, and injection force data.

20. The system of claim 17, wherein some or all of the received information is transmitted to a computing network and wherein said received information is analyzed and displayed to users of a computing network.

21. The system of claim 20, wherein some or all of the received information is analyzed on the computing system prior to transmission to the computing network.

22. The medical data collection system of claim 17 wherein the computing system
(i) has access to patient information,
(ii) communicates with the device of claim 1 to receive information concerning the drug or substance being administered and information concerning a patient,
(iii) accesses the drug and substance and patient information to retrieve information associated with the received information, and
(iii) provides some or all of retrieved information concerning the drug or substance being administered and the patient to a user via one or more of visual or audio components.

23. The system of claim 22, wherein said patient information resides on one or more of (i) a computing device or network in wireless or wired communication with the computing system or (ii) on the computing system itself.

24. The system of claim 22 wherein the received information is selected from a group consisting of: patient information, drug or substance identity, drug or substance administration requirements, drug or substance contraindications, injection pressure data, and injection force data.

25. The system of claim 22, wherein some or all of the received information is transmitted to a computing network and wherein said received information is analyzed and displayed to users of a computing network.

26. The system of claim 25 wherein some or all of the received information is analyzed on the computing system prior to transmission to the computing network.

* * * * *